United States Patent
Van Hegelsom

(12) 
(10) Patent No.: US 6,840,238 B1
(45) Date of Patent: Jan. 11, 2005

(54) ASSEMBLY FOR FIXING A TUBE FOR MEDICAL PURPOSES TO A PATIENT'S MOUTH

(76) Inventor: Johannes Alphonsus Van Hegelsom, Brouwersweg 19-7351, TJ Hoenderloo (NL)

(*) Notice: Subject to any disclaimer, the term of this patent is extended or adjusted under 35 U.S.C. 154(b) by 0 days.

(21) Appl. No.: 09/719,620
(22) PCT Filed: Jun. 14, 1999
(86) PCT No.: PCT/NL99/00369
§ 371 (c)(1), (2), (4) Date: Dec. 14, 2000
(87) PCT Pub. No.: WO99/65553
PCT Pub. Date: Dec. 23, 1999

(51) Int. Cl.[7] .............................................. A62B 18/00
(52) U.S. Cl. ........................... 128/201.22; 128/200.24; 128/207.14; 128/207.17; 128/DIG. 26
(58) Field of Search ................ 128/200.24, 200.26, 128/201.22–202.11, 201.24, 201.26, 207.14–207.18, DIG. 26, 200.14, 202.15, 204.18, 207.11, 206.29; 604/77, 264, 174, 179; 606/108

(56) References Cited

U.S. PATENT DOCUMENTS

| | | | |
|---|---|---|---|
| 3,976,080 A | 8/1976 | Bornhorst | |
| 4,249,529 A | 2/1981 | Nestor et al. | 128/207.17 |
| 4,270,529 A | 6/1981 | Muto | 128/200.26 |
| 4,744,358 A * | 5/1988 | McGinnis | 128/207.17 |
| 5,009,227 A * | 4/1991 | Nieuwstad | 128/207.17 |
| 5,076,269 A | 12/1991 | Austin | 128/207.17 |
| 5,345,931 A | 9/1994 | Battaglia, Jr. | 128/207.17 |
| 5,421,327 A | 6/1995 | Flynn et al. | 128/207.17 |
| 5,517,986 A | 5/1996 | Starr et al. | 128/205.25 |
| 5,555,881 A | 9/1996 | Rogers et al. | 128/207.17 |
| 5,623,924 A | 4/1997 | Lindenman et al. | 128/207.17 |
| 5,806,516 A * | 9/1998 | Beattie | 128/207.17 |
| 5,934,276 A * | 8/1999 | Fabro et al. | 128/207.17 |
| 6,067,985 A * | 5/2000 | Islava | 128/207.17 |

FOREIGN PATENT DOCUMENTS

| | | |
|---|---|---|
| DE | 3218368 | 11/1983 |
| WO | 9748432 | 12/1997 |

* cited by examiner

*Primary Examiner*—Glenn K. Dawson
(74) *Attorney, Agent, or Firm*—Ladas & Parry

(57) ABSTRACT

The invention relates to an assembly for fixing a tube for medical purposes to a patient's mouth, the tube being fixed to the patient's head. According to the invention the assembly comprises a tube clamping means which can be attached to the tube in a detachable manner, which tube clamping means is provided with positioning means connected thereto, which position the tube clamping means during use with the help of flexible, detachable securing means that are to be arranged around the patient's head, the tube clamping means being designed such that it can be clamped around the tube after arranging the tube in the patient's mouth without disturbing the location of the tube.

46 Claims, 3 Drawing Sheets

ASSEMBLY FOR FIXING A TUBE FOR MEDICAL PURPOSES TO A PATIENT'S MOUTH

The invention relates to an assembly for fixing a tube for medical purposes to a patient's mouth, the tube being fixed to the patient's head.

When anaesthetizing a patient an endotracheal tube or respiration tube has to be inserted in the patient's windpipe or a larynx mask has to be inserted in the patient's throat. After intubation the annular space between the tube and the windpipe has to be closed off so that the patient breathes only through the tube. This closing off is effected with a balloon, which is inflated after insertion. In order that the tube with the balloon is not moved in the windpipe, which could lead to damage of the windpipe, the tube has to be fixed to the patient's head.

Usually the tube is fixed with the help of a band aid and/or a ribbon. This, however, has the disadvantage that a band aid no longer adheres well when it becomes moist, and that when removing the band aid the skin could get damaged. When using a ribbon it has to be tied tightly around the neck, which results in pressure on the underlying structures and the possibility that the skin among others near the corners of the mouth can get cut in. A further disadvantage is that the band aid or the ribbon cannot be removed quickly. Danger of contamination is another drawback.

In U.S. Pat. No. 4,249,529 a tube clamp is shown, which with the help of two cords can be secured to the patient's head. The tube clamp comprises two semi-circular clamping members, which are attached to a plate via arms that are inclined towards each other and which are connected to each other by means of a hinge. The tube is clamped by pressing both clamping members in a direction opposite to the coinciding component of the arms, as a result of which the clamping members hinge towards each other into a closing position. This activity is rather difficult to control, as a result of which a longitudinal displacement of the tube during the process of letting it clamp is possible here. Also the track over which the tube has to be moved in transverse direction is substantial, because of which the danger of displacement only increases. The result may be that the tube, of which the anaesthetist had first noticed that its end was correctly situated near the fork of the lungs, moves to such an extent that it extends in one of the lungs with one end. The other lung is then sidetracked, which entails major risks for the patient during the operation. Moreover, the efficiency of the balloon closing may be insufficient.

From the literature several other devices are known to fix an endotracheal tube to the patient's head. None of these known constructions, however, offers a satisfactory solution in practice. In particular the ease of placing and quick removal of the device are not achieved.

It is an object of the invention to provide an assembly for fixing a tube for medical purposes in a patient's mouth, which can easily and reliably be placed by the anaesthetist. It is another object of the invention to provide an assembly which can quickly be removed from the tube. It is yet another object to provide an assembly which can partly be arranged on the patient's head in advance. It is a further object of the invention to provide an assembly which after being used once can be disposed of. It is yet a further object of the invention to provide an assembly which can be made in a simple and cheap manner. These and further objects appear from the description below.

One or more of these objects are achieved with an assembly for fixing a tube for medical purposes to a patient's mouth, the tube being fixed to the patient's head, comprising a tube clamping means which can be attached to the tube in a detachable manner, which tube clamping means is provided with first positioning means, further comprising flexible, detachable securing means that are to be arranged around the patient's head and are provided with second positioning means that can be connected to the first positioning means, to position the tube clamping means during use, the tube clamping means comprising a first tube clamping member, which is solid with the first positioning means, and a second tube clamping member, which is hingeable with respect to the first tube clamping member for movement between an open position, in which the tube clamping means can freely receive the tube, and a closed clamping position, in which the tube is kept clamped with respect to the tube clamping means and the first positioning means.

The tube clamping means need not be arranged until after the patient has been intubated. With the help of detachable securing means and the second positioning means the tube clamping means can be positioned by means of the first positioning means, the first clamping member solid therewith stabilizing the tube to be clamped during clamping. The anaesthetist can focus his attention to rotating the single other clamping member. In this manner unwanted tube displacements which may be damaging to the patient, can be prevented.

Preferably the first tube clamping member is arranged in order to extend under the tube during use, so that this clamping member constitutes as it were a bearing for the tube that is not (entirely) clamped yet.

Preferably the two tube clamping members are formed by two half oval rings, which along one edge are connected to each other by means of a hinge, preferably a living hinge. It is furthermore preferred when the first and the second tube clamping members are hingeable about an axis which is substantially parallel to the tube to be clamped.

Preferably the two tube clamping members are securable to each other in their clamping position by means of catching means, preferably comprising a snap finger at the one clamping member and a cam at the other clamping member, the snap finger then being detachably snappable behind the cam. In this way the tube clamping means can be closed and opened in an easy and therefore controllable manner.

In the unlikely event of a tube being used that does not exactly fit, fixation against axial displacement of the tube is improved when both tube clamping members are provided at their insides with a number of inwardly directed tube fixation protrusions. With the help of these fixation protrusions the clamped tube is held additionally and cannot be pulled through the tube fixation means.

Preferably one of the tube clamping means is provided with a recess for letting through a pilot tube (for supply and discharge of air to and from the balloon sleeve) on the tube, so that the pilot tube cannot be clamped off. It is preferred here when the first tube clamping member is provided with a continuous recess, which extends, at least at the outer end of the clamping member, over its entire wall cross-section. It is prevented in this way that with a curved tube the pilot tube is pressed closed as yet at the outer end of the clamping member. This is of vital importance. When the balloon sleeve is insufficiently inflated namely, a part of the stomach contents may end up in the lung. On the other hand, when the sleeve remains inflated to hard, tissue damage resulting in scars may occur.

According to an advantageous embodiment the tube clamping member is entirely made from synthetic, preferably from polypropene. As a result the tube clamping means can easily and cheaply be manufactured by injection moulding, as a result of which it can be used as a disposable product. Also the material is well adjusted to the human body. The clamping members in themselves are relatively rigid.

Preferably the hinge is a living hinge, so that the hinge can be made during injection moulding without additional measures being necessary. In this way the tube clamping means remains cheap.

Preferably the first positioning means are provided on a plate which is substantially transverse to the tube clamping means, which plate preferably is provided with a slot to let the tube through when arranging the plate, the plate preferably being substantially U-shaped. With the help of the plate the tube clamping means can easily be placed at the patient's head, whereas the plate further provides good support against the patient's head.

Preferably the first positioning means comprise-preferably vertical-slots, for letting through attachment straps belonging to the second positioning means. For optimal transfer of forces thus four slots can be arranged in the plate, mainly at the vertices of a rectangle.

According to a preferred embodiment the plate is adapted to the anatomy of the patient's face, so that the pressure on the patient's face can never become to high.

Preferably a bite member for between the patient's teeth is provided at the rear of the plate. Because of this bite member the patient will not accidentally be able to bite in the tube, as a result of which the passage opening becomes too small and the tube could get damaged.

Preferably the bite member is substantially U-shaped in cross-section to allow the tube through. The U-shaped bite member connects to the U-shaped plate, so that the whole can be slid around the tuba from the chin side after which the tube clamping means can be clamped around the tube. After detaching the tube clamping means the plate with the bite member can easily be removed again.

Preferably the bite member and the plate are provided with concave surfaces and edges, respectively, at their sides, so that as much room as possible is left to get into the mouth, for instance with medical instruments.

Preferably the plate and the bite member are provided with recesses aligned with the aforementioned recess for allowing through a pilot tube on the tube. The recess in the bite member can be continuous over the entire length and its wall cross-section, so that the pilot tube has ample possibilities to extend into the mouth in an unclamped manner.

According to a further development the second positioning means comprise an occipital strap and a number of flexible, detachable attachment straps extending between the occipital strap and the first positioning means. With the-flat-strap around the head and the-flat-adjustable straps the plate with the tube clamping means can be positioned and kept in place well, with a correctly adjustable tightness of the straps around the head. The straps are soft and do not adhere to the user's head, so that the skin will not be damaged or cut in.

Preferably the straps that are adjustable as to length run through the recesses in the plate and they can be secured on themselves. The straps adjustable as to length are thus attached to the plate and do not need to be separately arranged.

According to another preferred embodiment the straps adjustable as to length are accommodated to the plate when said plate is manufactured. For instance when injection moulding the plate the ends of the straps can be laid in the matrix, after which the plate is formed around the ends.

Preferably the straps adjustable as to length can be adjustable as to length by means of Velcro.

Preferably each strap that is adjustable as to length is connected to the plate on two locations and has a recess in between them. As a result of the connection on two locations on both sides the plate can be positioned in a very stable manner, and because of the recesses in the straps the inside of the mouth can still be reached along the plate.

The occipital strap in an advantageous manner is provided at both ends with a recess to let through the ends of the attachment straps that are adjustable as to length, the occipital strap-in order to have the straps abut tightly and in a flat manner-preferably being provided with means for stiffening the recesses, such as a little rod extending along the recess, said rod preferably being situated at the side of the recess facing the attachment strap. In this way the occipital strap remains tight there and the forces are transferred better. Quickly untying in case of an emergency is also improved.

For an optimal transfer of forces the recesses are situated at the level of is the corners of the jaw. The forces are then transferred, at least for the larger part, on the jaw corner and deflected upwards for a small part, via the temple. This is much more comfortable for the patient and better for the blood circulation, because there is no pressure on the blood vessels below and adjacent to the jaw. In addition these areas are then free for insertion of monitor lines, such as for instance in the neck.

Preferably the occipital strap is accommodated in a hat or cap to be placed over the patient's head. In this way the occipital strap is immediately in the correct place after arranging the cap or hat, and the strap cannot be displaced during use. The cap does not only give ease and certainty of placement, it also performs a function in counteracting the loss of warmth through evaporation and radiation. Usually the loss of warmth via the head is about 20–30%. The cap thus provides a passive means for keeping the body at the right temperature.

Preferably the strap also runs along the lower side of the patient's ears during use.

Preferably the hat is provided with recesses for the patient's ears, so that ear operations and the like can be performed. Moreover the blood saturation of the ears is ensured. The position of the ears can also be checked, which is of importance when the patient is lying with his ear on a pillow. One is then able to see from aside whether the ear is in the correct position. This is of importance, because the ears are end organs and may die off in a situation in which they are pinched off. Another advantage is that measuring can now still be performed on the ear, for instance a pulsoxy meter, for assessing the blood circulation.

The cap can be arranged in advance. The attachments for the mouthpiece are situated on the side, so that without moving the patient's head the mouthpiece can be attached with the help of the Velcro strips.

The cap can furthermore fulfill another function, when it extends over the head and at the front/upper side is provided with means for attachment of either care or monitor lines. The cap thus also provides surfaces available for securing catheters/probes and other lines. In this manner a drip line can be arranged in the neck, said line being attached on the side of the cap. Stomach and temperature probes can be laid over the head towards the nose, and be secured on top of the cap with the help of the Velcro strips.

The invention furthermore relates to a tube clamping means suitable for the assembly of the invention, as well as to the above-mentioned hat or cap.

The invention will be elucidated on the basis of an exemplary embodiment, referring to the attached drawing.

FIG. 1 schematically shows a patient, the assembly according to the invention being used and the assembly comprising schematically shown tube clamping means, positioning means and attachment means.

Figure 1:
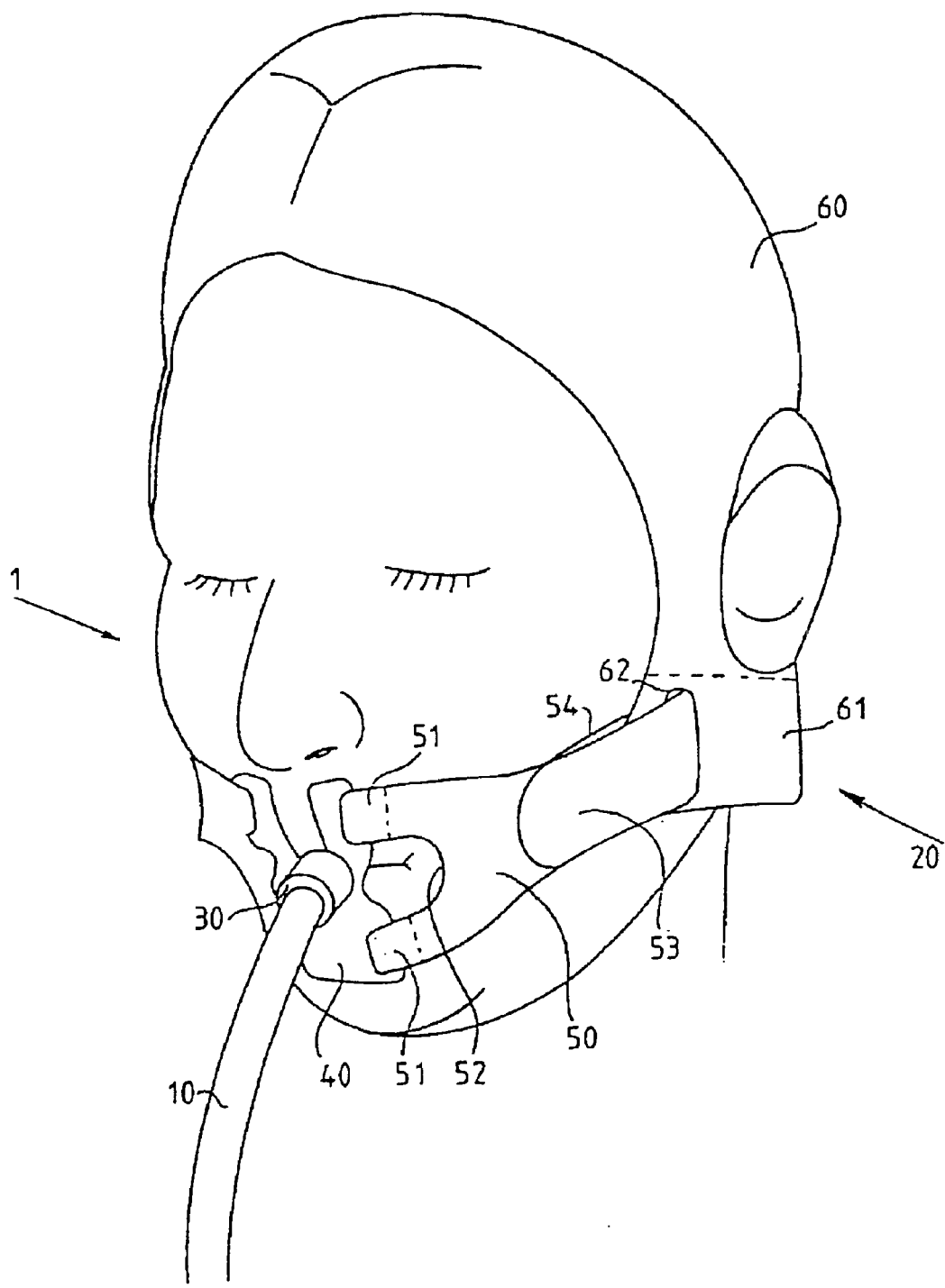

FIG. 1 schematically shows the patient's head 1, a respiration tube 10 being inserted in the windpipe through the patient's mouth. Around the patient's head 1 an assembly 20 is arranged for fixing the respiration tube 10. The assembly 20 consists of a tube clamp 30, a positioning plate 40, two attachment straps 50, and a pulling strap 61 which is accommodated in a cap 60.

Figure 2:
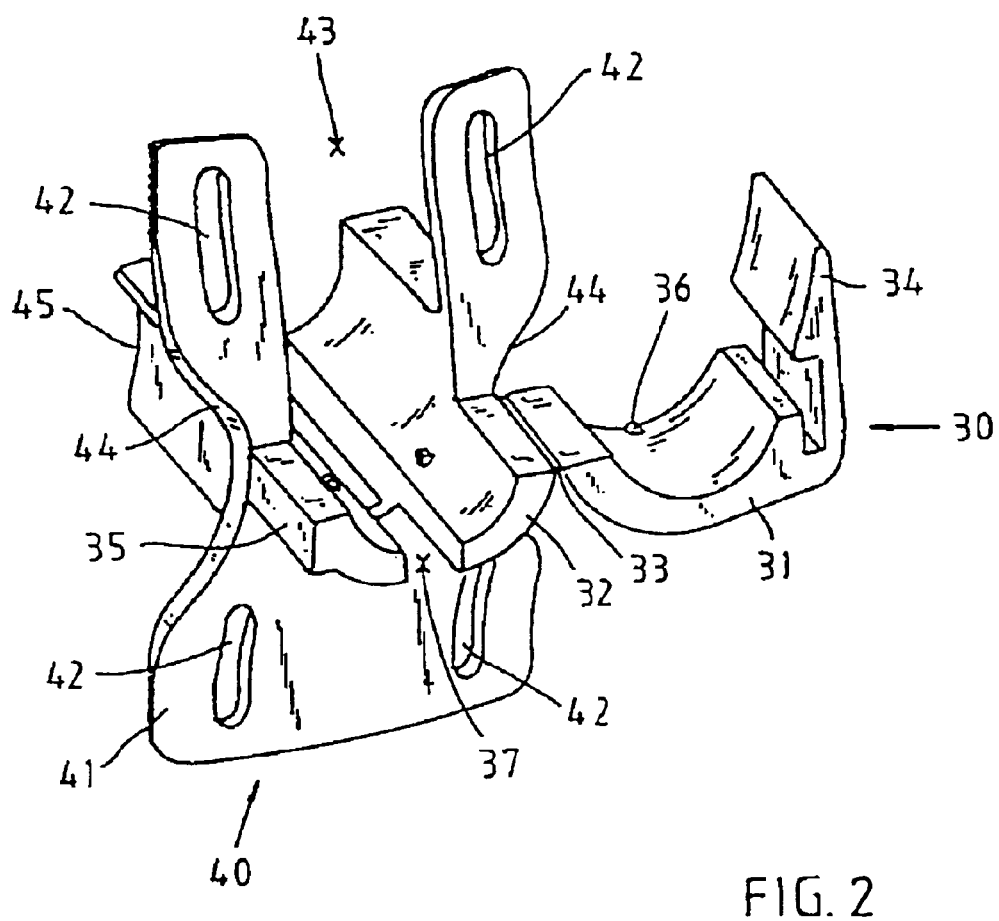
FIG. 2 shows the tube clamping means according to the invention in perspective view.
Figure 3:
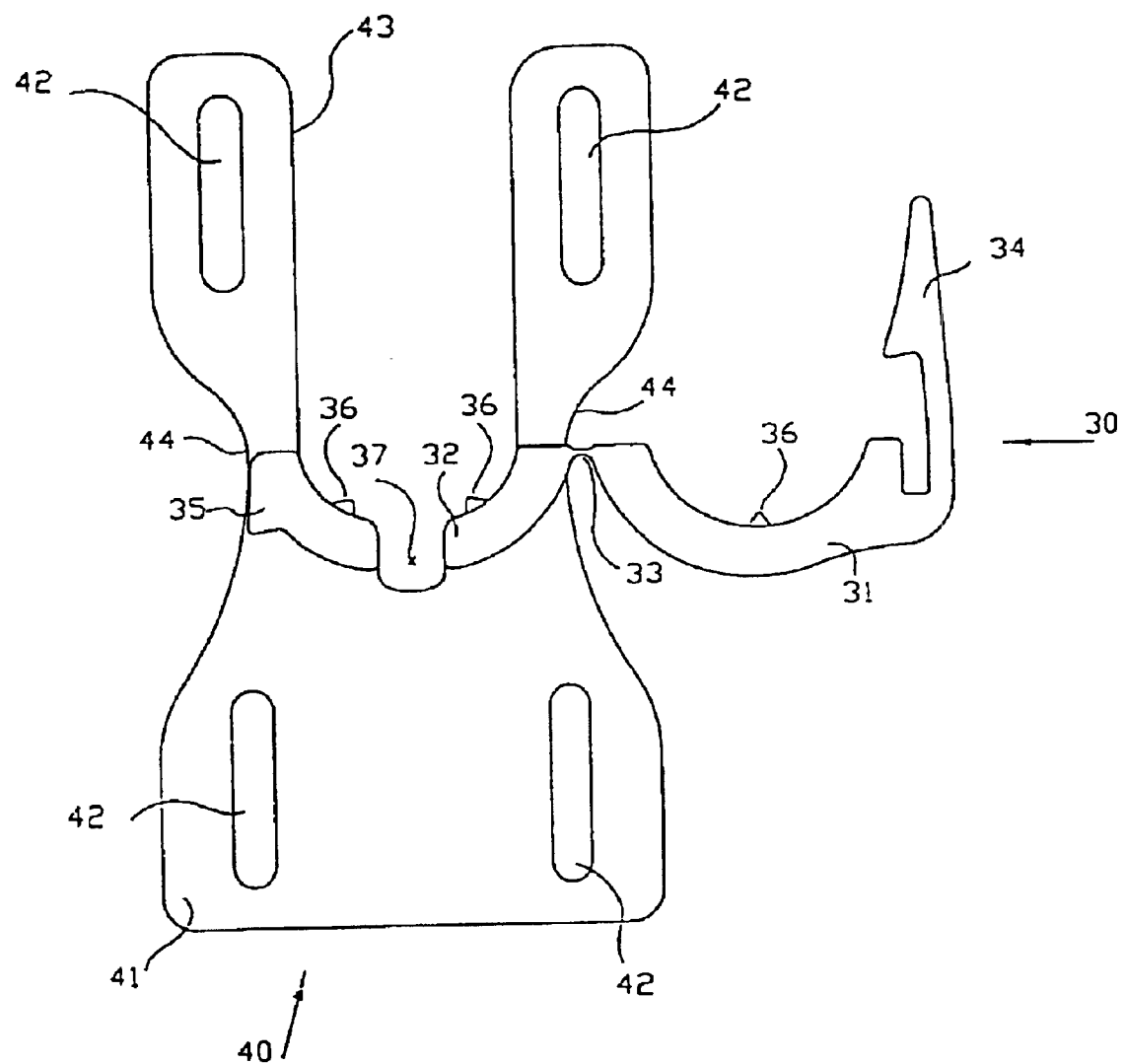
FIG. 3 shows the tube clamping means according to FIG. 2 in front view.

The tube clamp 30 and the positioning plate 40 are shown in more detail in FIGS. 2 and 3.

FIG. 2 shows the tube clamp 30 and the positioning plate 40 in perspective view. The tube clamp 30 consists if a moveable half oval ring 31 which can be moved with respect to a half oval ring 32 which is solid with the plate 40, in which both half oval rings are connected to each other by means of a living hinge 33. The movable half oval ring 31 has a snap finger 34, which can hook about a cam 35 on the solid half oval ring 32. The snap finger 34 is elastic in order to remove the snap finger 34 from the cam 35, so that the half oval ring 31 can be opened with respect to the half oval ring 32. Both half oval rings 31 and 32 are of such a size that they can clamp the respiration tube 10 between them in the closed position of the tube clamp 30. The inside of the member 31 is provided with a fixation protrusion 36, and the inside of the solid member 32 is provided with two fixation protrusions to additionally fix the respiration tube 30 in longitudinal direction, in addition to the frictional forces. The solid half oval ring 32 is provided with a recess 37 extending transverse through the wall in order to accommodate a pilot tube (see 73, FIG. 1), which runs along the respiration tube 10, for a large part loose at the concave bent lowerside thereof, without pressing the pilot tube closed.

The positioning plate 40 consists of a plate member 41 of a substantially rectangular shape, four vertical slots 42 being arranged in the corners, for the attachment of the attachment straps 50 (see FIG. 1). The plate member 41 is provided with a U-shaped slot 43 to let the respiration tube 10 through to the tube clamp 30 and is provided with recesses 44 on both sides, so that the plate member 41 leaves sufficient space around the respiration tube 10 after arrangement to get into the patient's mouth with for instance medical instruments. At the rear of the plate member 41 a bite member 45 is arranged which is formed as one unity therewith, which bite member is in line with the half oval ring 32 and which is provided with a U-shaped recess in order to accommodate the respiration tube 10, so that the tube 10 cannot be squeezed together by the patient's teeth. The bite member 45 is provided with recesses at the sides which connect to the recesses 44 in the plate member 41.

As can be seen in FIGS. 2 and 3 the recess 37 is continued in the plate member 41 and the bite member 45, the recess 37 also extending through the entire wall thickness in the bite member.

FIG. 3 shows the parts of the tube clamp 30 and the positioning plate 40 in front view.

The tube clamp 30, the positioning plate 40 and the bite member 45 are manufactured as one unity from a suitable synthetic, such as polypropene. The mouthpiece, consisting of the tube clamp 30, the positioning plate 40 and the bite member 45 can then be made by means of injection moulding.

Polypropene here has the advantage that it can be made transparent, so that the information on the respiration tube 10 can still be read.

The attachment straps 50 have two fingers 51 at one end, which are separated by a recess 52. The attachment straps 50 are made from a flexible, soft material such as Medifoam®, and the fingers 51 are pulled through the slots 52 in the positioning plate 41 and turned and secured on themselves, for instance by sewing. Because of the recesses 52 it is possible to get into the patient's mouth for instance with medical instruments. The other end of the attachment straps 50 is provided with Velcro, the last part 43 for instance being provided with looped tape, and the part preceding it being provided with barbed tape.

The assembly further consists of a cap 60, which fits rather closely to the patient's head 1, and which leave the patient's ears free. At the lower edge of the cap 60 an occipital strap or pulling strap 61 is accommodated in the cap 60, which pulling strap 61 can run underneath the patient's ears behind the patient's head and which pulling strap 61 is provided with a slot 62 at its ends where the part 53 of the attachment strap 50 can be inserted through. At the front side of the slot 62 a little rod is accommodated in the material of the cap 60, in order to maintain the shape of the slot 62 and to distribute the forces better.

The use of the assembly is as follows.

The hat can already be placed on the patient's head during the preparations of the operation. Subsequently the respiration tube 10 is arranged in the patient's windpipe. When said respiration tube 10 is positioned correctly, the positioning plate 40 is slid around the tube 10, the U-shaped recess 43 moving around the tube 10, until the tube 10 lies in the half oval ring 32. The pilot tube 73 then extends downwards through the recess 37 free from the tube. The bite member 45 is placed between the patient's teeth. The ends 53 of the attachment straps 50 are inserted through the slots 62 in the pulling strap 61, and the ends 53 are pulled such and folded down to such an extent that the pulling strap 61 is brought at the right tension. Subsequently the strap portion 53 with looped tape is attached on the strap portion 54 with barbed tape. The positioning plate 40 is fixed on the patient's head in that way. Finally the respiration tube 10, after the anaesthetist has ascertained that its end is situated in the correct location, is fixed in the tube clamp 30 by rotating the half oval ring 31 to the solid half oval ring 32 and then to secure it with the snap finger 34 about the cam 35.

The advantage of fixing in this order is that the movements of the respiration tube 10 can be kept limited to a minimum in this way.

The advantage of the cap 60 is that from a hygienic point of view it retains the hair, and ensures that the pulling strap 61 cannot slide down from the jaw corner to the neck. Furthermore cooling down of the head is counteracted. It is further expected that a patient will have less objections to a cap than to just wearing a pulling strap. The cap 60 can furthermore be useful in securing care lines, such as the stomach catheter 72, which with the help of Velcro 71 cooperating with the Velcro surface 70 on the cap 60 can be secured (see FIG. 1).

The assembly is easy to detach by operating the snap finger 34 and pulling the Velcro loose from the portion 53. In case of an emergency the respiration tube 10 can be detached from the patient with the mouthpiece still on it, just by untying the Velcro on both sides.

What is claimed is:

1. An assembly for fixing a tube to a patient's mouth for medical purposes, the assembly comprising tube clamping means for detachably clamping the tube with the tube fixed to the patient's head, the tube clamping means comprising (a) first positioning means for positioning the tube,
(b) a first tube clamping member,
(c) a second tube clamping member; and
(d) means for hingeable movement of the second tube clamping member with respect to the first tube clamping member wherein said first positioning means has a top portion that extends above a top portion of the first and second tube clamping members and a bottom portion that extends below a bottom portion of the first and second tube clamping members, said first tube clamping member being fixedly disposed with respect to the first positioning means and having a concave bearing surface which curves toward the top portion of the first positioning means, and wherein the second tube clamping member is moveable between a closed clamping position, in which the tube is kept clamped between the first and second tube clamping members with the first tube clamping member extending under the tube, and an open position, in which the tube clamping means can freely receive the tube and the tube can find support on the concave bearing surface of the first tube clamping member, without movement of the first tube clamping member relative to the first positioning means, the assembly further comprising securing means for detachably securing the assembly around the patient's head, said securing means comprising second positioning means for connecting the securing means to the first positioning means to facilitate positioning of the tube clamping means.

2. The assembly according to claim 1, wherein the first positioning means comprises a positioning plate which is substantially transverse to the first and second tube clamping members and is integrally formed with the first clamping member.

3. The assembly according to claim 2, wherein the positioning plate comprises a slot for the tube.

4. The assembly according to claim 3, wherein the positioning plate is substantially U-shape.

5. The assembly according to claim 2, wherein the first positioning means comprises a plurality of slots for attachment straps of the second positioning means, four of the slots being disposed in the plate in a rectangular configuration.

6. The assembly according to claim 2, wherein the positioning plate is adapted to conform to the patient's face.

7. The assembly according to claim 2, wherein the positioning plate comprises a bite member at a rear portion thereof for positioning between teeth of the patient.

8. The assembly according to claim 7, wherein the first tube clamping member comprises a continuous recess that, at least at an outer end of the first tube clamping member, extends over an entire cross-section of the first tube clamping member, whereby to accommodate a pilot tube, the positioning plate and the bite member comprising recesses that are aligned with the continuous recess for the pilot tube, the recess in the bite member being continuous over an entire length and cross-section of the bite member.

9. The assembly according to claim 7, wherein the bite member is substantially U-shape in cross-section.

10. The assembly according to claim 7, wherein the bite member and the positioning plate comprise respective concave surfaces and edges at sides thereof.

11. The assembly according to claim 1, wherein the second positioning means comprises an occipital strap and a plurality of flexible, detachable attachment straps that extend between the occipital strap and the first positioning means, the occipital strap comprising slots for the attachment straps, the second positioning means comprising means for adjusting the attachment straps as to length whereby the attachment straps can be secured to themselves on both sides of the patient's head with the such that, after the tube is clamped between the first and second tube clamping members, the tube can be fixed to the patient's head.

12. The assembly according to claim 11, wherein the first positioning means comprises a positioning plate which is substantially transverse to the first and tube clamping members and which is integrally formed with the first tube clamping member, the attachment straps being connected to the positioning plate.

13. The assembly according to claim 11, wherein the means for adjusting the attachment straps as to length comprises velcro.

14. The assembly according to claim 11, wherein each of the attachment straps is connected to the plate at a plurality of locations and has a recess between the plurality of locations.

15. The assembly according to claim 11, wherein the occipital strap comprises means for stiffening the slots.

16. The assembly according to claim 15, wherein the means for stiffening comprises a rod extending along a side of the slot.

17. The assembly according to claim 11, wherein the slots are adapted to be disposed at a level with corners of a jaw of the patient with the assembly adapted to fix the tube to the patient's mouth.

18. The assembly according to claim 11, wherein the occipital strap is accommodated in a cap for placement over the patient's head.

19. The assembly according to claim 18, wherein the cap comprises recesses for the patient's ears.

20. The assembly according to claim 18, wherein the cap is adapted to extend over the patient's head with the assembly adapted to fix the tube to the patient's mouth, the cap comprising means for attachment of care or monitor lines at a front or upper side thereof.

21. The assembly according to claim 1, wherein the means for hingeable movement provides for hingeable movement of the second tube clamping member about an axis that is substantially parallel to the tube when the tube is received in the tube clamping means.

22. The assembly according to claim 21, wherein each of the first and second tube clamping members comprises a half oval ring, the means for hingeable movement comprising a hinge, the half oval ring of each of the first and second tube clamping members being connected to each other by the hinge.

23. The assembly according to claim 1, comprising catching means for securing the first and second tube clamping members to each other with the second tube clamping member in the closed clamping position.

24. The assembly according to claim 23, wherein the first and second tube clamping members collectively comprise snap finger and cam means for detachably snapping the second tube clamping member to the first tube clamping member with the first and second tube clamping members in the closed clamping position.

25. The assembly according to claim 1, wherein each of the first and second tube clamping members comprises a protrusion that protrudes inwardly for fixing the tube.

26. The assembly according to claim 1, wherein the first positioning means comprises a plurality of slots for attachment straps of the second positioning means.

27. The assembly according to claim 26, wherein the slots are aligned.

28. The assembly according to claim 1, wherein the first tube clamping member comprises a continuous recess that, at least at an outer end of the first tube clamping member, extends over an entire cross-section of the first tube clamping member, whereby to accommodate a pilot tube.

29. The assembly according to claim 1, wherein the tube clamping means comprises a synthetic material.

30. The assembly according to claim 1, wherein said first tube clamping member is integrally formed with the first positioning means whereby it maintains its position with respect to the first positioning means during movement of the second tube clamping member between said open and closed positions.

31. The assembly according to claim 1, wherein the second positioning means comprises an occipital strap which is accommodated in a cap for placement over the patient's head.

32. The assembly according to claim 1, wherein the first positioning means has top a portion that extends above the first and second tube clamping members, the top portion comprising first and second parts defining an opening disposed above the concave bearing surface and extending throughout the top portion whereby a tube can be inserted from above the top portion between the first and second parts and onto the concave bearing surface.

33. The assembly according to claim 1, wherein said assembly comprises a bite member having a concave bearing surface that is conterminous with the concave bearing surface of the first tube clamping member, with the second tube clamping member covering only the concave bearing surface of the first tube clamping member in the closed clamping position.

34. A method for fixing a tube to the mouth of a patient comprising the steps of:
  (i) providing the assembly of claim 1;
  (ii) clamping the tube in the tube clamping means, with the securing means secured to the patients head and with the tube fixed to the patient's head, by moving the second tube clamping member between the open position and the closed clamping position with the first tube clamping member fixed to the first position means; wherein the top portion of the first positioning means extends above a top portion of the first and second tube clamping members and above lips of the patient and a bottom portion of the first positioning means extends below the first and second tube clamping members and below the lips of the patient.

35. An assembly for fixing a tube to a patient's mouth for medical purposes, the assembly comprising
  tube clamping means for detachably clamping the tube with the tube fixed to the patient's head, the tube clamping means comprising
    (a) first positioning means for positioning the tube,
    (b) a first tube clamping member,
    (c) a second tube clamping member; and
    (d) means for hingeable movement of the second tube clamping member with respect to the first tube clamping member,
    wherein said first positioning means has a portion that extends above the first and second tube clamping members, and a portion that extends below the first and second tube clamping members, when the tube is fixed to the patient's mouth, and the second tube clamping member is moveable between a closed clamping position, in which the tube is kept clamped between the first and second tube clamping members with the first tube clamping member extending under the tube, and an open position, in which the tube clamping means can freely receive the tube and the tube can be supported on the first tube clamping member, which provides an upwardly facing bearing surface for the tube, without movement of the first tube clamping member relative to the first positioning means,
  the assembly further comprising securing means for detachably securing the assembly around the patient's head, said securing means comprising second positioning means for connecting the securing means to the first positioning means to facilitate positioning of the tube clamping means.

36. The assembly according to claim 35, wherein the second positioning means extends above and below said tube.

37. The assembly according to claim 36, wherein said second positioning means comprises an upper second positioning means that extends above said tube, and a lower second positioning means that extends below said tube.

38. An assembly for fixing a tube to the mouth of a patient for medical purposes, the assembly comprising
  tube clamping means for detachably clamping the tube to fix to the patient's head, the tube clamping means comprising
    (a) first positioning means for positioning the tube,
    (b) a first tube clamping member,
    (c) a second tube clamping member; and
    (d) means for hingeable movement of the second tube clamping member with respect to the first tube clamping member, said first tube clamping member being fixedly disposed with respect to the first positioning means, and said second tube clamping member being moveable between a closed clamping position, in which the tube is kept clamped between the first and second tube clamping members with the first tube clamping member extending under the tube, and an open position, in which the tube clamping means can freely receive the tube and the tube can find support on the first tube clamping member,
  the assembly further comprising securing means for detachably securing the assembly around the patient's head, said securing means comprising second positioning means for connecting the securing means to the first positioning means to facilitate positioning of the tube clamping means, wherein the second positioning means comprises an occipital strap, wherein the occipital strap is accommodated in a cap for placement over the patient's head.

39. The assembly according to claim 38, wherein the cap comprises recesses for the patient's ears.

40. The assembly according to claim 38, wherein the cap is adapted to extend over the patient's head and the assembly is adapted to fix the tube to the patient's mouth, the cap comprising means for attachment of care or monitor lines at a front or upper side thereof.

41. The assembly according to claim 38, wherein the second positioning means comprises a plurality of flexible, detachable attachment straps that extend between the occipital strap and the first positioning means, the occipital strap comprising slots for the attachment straps, the second positioning means comprising means for adjusting the attachment straps as to length whereby the attachment straps can be secured to themselves on both sides of the patient's head.

42. The assembly according to claim 41, wherein the means for adjusting as to length comprises velcro.

43. The assembly according to claim 41, wherein each of the attachment straps is connected to the plate at a plurality of locations and has a recess between the plurality of location.

44. The assembly according to claim 41, wherein the occipital strap comprises means for stiffening the slots.

45. The assembly according to claim 44, wherein the means for stiffening comprises a rod extending along a side of the slot.

46. The assembly according to claim 41, wherein the slots are adapted to be disposed at a level with corners of a jaw of the patient with the assembly adapted to fix the to the patient's mouth.

* * * * *

UNITED STATES PATENT AND TRADEMARK OFFICE
CERTIFICATE OF CORRECTION

PATENT NO.    : 6,840,238 B1  
DATED         : January 11, 2005  
INVENTOR(S)   : Johannes Alphonsus Van Hegelsom Page 1 of 1

It is certified that error appears in the above-identified patent and that said Letters Patent is hereby corrected as shown below:

<u>Title page,</u>  
Item [30], insert:  
-- [30]    Foreign Application Priority Data,  
Jun. 18, 1998  (NL) ................................. 1009440 --.

Signed and Sealed this

Nineteenth Day of April, 2005